United States Patent
Sapia (10) Patent No.: US 7,633,531 B2
(45) Date of Patent: Dec. 15, 2009

(54) SYSTEMS AND METHODS FOR QUANTITATIVELY ASSESSING THE QUALITY OF AN IMAGE PRODUCED BY AN IMAGING SYSTEM

(75) Inventor: Mark A. Sapia, Canton, CT (US)

(73) Assignee: General Electric Company, Schenectady, NY (US)

( * ) Notice: Subject to any disclaimer, the term of this patent is extended or adjusted under 35 U.S.C. 154(b) by 382 days.

(21) Appl. No.: 11/618,829

(22) Filed: Dec. 31, 2006

(65) Prior Publication Data

US 2008/0158374 A1    Jul. 3, 2008

(51) Int. Cl.
 *G01N 21/00* (2006.01)
 *H04N 5/228* (2006.01)
 *G21C 17/00* (2006.01)
(52) U.S. Cl. ............... 348/222.1; 356/237.1; 376/248; 376/249; 348/218; 250/201.9
(58) Field of Classification Search ............ 356/237.1, 356/614–615; 348/222.1, 218, 335, 340; 250/201.9, 214 VT; 376/248, 249
See application file for complete search history.

(56) References Cited

U.S. PATENT DOCUMENTS

| | | | |
|---|---|---|---|
| 4,870,692 A * | 9/1989 | Zuiderveld et al. | 382/107 |
| 4,941,106 A * | 7/1990 | Krieger | 700/259 |
| 5,306,907 A * | 4/1994 | Nudelman et al. | 250/214 VT |
| 5,448,053 A * | 9/1995 | Rhoads | 250/201.9 |
| 5,774,179 A * | 6/1998 | Chevrette et al. | 348/218.1 |
| 5,912,933 A | 6/1999 | Shaug et al. | |
| 5,912,934 A * | 6/1999 | Acks et al. | 376/248 |
| 6,477,218 B1 | 11/2002 | Fukasawa | |
| 6,535,568 B1 | 3/2003 | Reese | |
| 6,553,090 B2 | 4/2003 | Fukasawa | |
| 6,664,734 B1 * | 12/2003 | Jasper, Jr. | 315/3.5 |
| 6,744,840 B2 | 6/2004 | Karino et al. | |
| 6,748,348 B1 | 6/2004 | Russell | |
| 6,862,329 B1 | 3/2005 | Kropaczek et al. | |
| 7,245,755 B1 * | 7/2007 | Pan et al. | 382/131 |
| 2003/0086520 A1 | 5/2003 | Russell et al. | |
| 2003/0128793 A1 | 7/2003 | Karino et al. | |
| 2004/0101083 A1 | 5/2004 | Russell et al. | |
| 2004/0122629 A1 | 6/2004 | Russell et al. | |
| 2004/0122632 A1 | 6/2004 | Kropaczek et al. | |
| 2004/0236544 A1 | 11/2004 | Russell et al. | |

(Continued)

OTHER PUBLICATIONS

United States Nuclear Regulatory Commission Standard Review Plan, SRP-15.0.1, Jul. 2000.

(Continued)

*Primary Examiner*—Sang Nguyen
(74) *Attorney, Agent, or Firm*—Harness, Dickey & Pierce, P.L.C.

(57) ABSTRACT

Methods and systems for quantitative image quality assessment of an imaging system, such as an in vessel visual inspection system, having a target, an image capture device and a computer. The target includes one or more image features with varying spatial resolutions and predetermined spatial frequencies. The image capture device is configured to capture an image of the target. The computer includes a processor, a memory, and computer executable instructions. The computer is configured to receive the captured image, prepare one or more intensity profiles across the captured image responsive to the predetermined spatial frequencies, and determine a modulation transfer function responsive to the one or more intensity profiles.

32 Claims, 6 Drawing Sheets

U.S. PATENT DOCUMENTS

| | | |
|---|---|---|
| 2005/0089831 A1 | 4/2005 | Russell et al. |
| 2005/0222833 A1 | 10/2005 | Kropaczek et al. |
| 2006/0149514 A1 | 7/2006 | Kropaczek et al. |
| 2006/0149515 A1 | 7/2006 | Horton et al. |
| 2006/0171499 A1 | 8/2006 | Farawila et al. |

OTHER PUBLICATIONS

NRC: Bulletin 79-26: Boron Loss from BWR Control Blades, U.S. Nuclear Regulatory Commission, IE Bulletin No. 79-26, Nov. 20, 1979.

NRC: Regulatory Guide 1.183—Alternative Radiological Source Terms for Evaluating D, Jul. 2000.

Eidolon Production Nodal Slide MTF Measurement System, Eidolon Optical, LLC, Aug. 25, 2004. www.eidolon-optical.com.

Understanding image Sharpness Part I: Introduction to resolution and MTF curves, Norman Koren, Mar. 7, 2004.

The Contrast Sensitivity Function (CSF), USD Internet Psychology Laboratory, Sep. 8, 2003. www.usd.edu/coglab/CSFIntro.htm.

RLG DigiNews: vol. 2, No. 1, Feb. 15, 1998. http://www.rlg.org/preserv/diginews/diginews21.html.

How to Measure MTF and other Properties of Lenses, Optikos Corporation, Jul. 16, 1999.

Resolution, Contrast, MTF, Lars Kjellberg, Nov. 12, 1998. http://old.photodo.com/art/Reso8.shtml.

Elements of Image Quality, Video Engineering, Third Edition (1999), A. Luther et al., http://www.optics.Arizona.edu.Detlab/Classes/OPTI%20563/Lecture%20Notes/Hans/Luther_Inglis_04.pdf.

* cited by examiner

SYSTEMS AND METHODS FOR QUANTITATIVELY ASSESSING THE QUALITY OF AN IMAGE PRODUCED BY AN IMAGING SYSTEM

FIELD

The present disclosure relates to imaging systems and, more specifically, to nuclear reactor in-vessel visual inspection (IVVI) imaging systems.

BACKGROUND

The statements in this section merely provide background information related to the present disclosure and may not constitute prior art.

Nuclear plant operators and service companies perform in vessel visual inspections (IVVI) in conjunction with reactor refueling operations to inspect various reactor components for flaws or damage to the reactor vessel and components within the reactor including submerged pipes and bores. For example, a reactor pressure vessel (RPV) of a boiling water reactor (BWR) typically has submerged bores that need to be inspected during maintenance routines. Hollow tubular jet pumps having internal bores are positioned within an annulus to provide the required reactor core water flow. During operation of the reactor, components including their weld joints within the reactor can experience inter-granular stress corrosion cracking (IGSCC) and irradiation assisted stress corrosion cracking (IASCC) which can diminish the structural integrity of the reactor components, such as jet pumps, by way of example. It is important to examine the reactor core components and all welds contained therein periodically to determine whether any cracking or failure has occurred.

The ability to accurately and quickly perform the IVVI visual inspections can impact the outage associated with the nuclear reactor and therefore improvements to the accuracy and speed with which visual inspections can be performed can reduce the outage period and save the nuclear plant operator significant expense.

A visual inspection system typically includes one or more camera positioned on a remotely operated vehicle that is positionable within the reactor vessel. Each camera is coupled to a video transmission system that provides an image signal to a remotely located visual display device or storage system. These visual systems are used to inspect the reactor components for flaws or damage and to look for debris that may have accumulated in the reactor. A variety of cameras are used for various tasks including inspections of the outer surface of pipes and inner bores of pipes, apertures and bores. Generally, each visual inspection system (camera, transmission system, and display) is required to meet predefined imaging standards to ensure that the visual inspection is capable of identifying and delineating the necessary specificity in flaw and damage identification. The requirements for IVVI visual inspection systems include visual Testing (VT) standards such as a rigorous EVT-1 standard, by way of example. The EVT-1 standard provides that the imaging system be capable of resolving a 0.0005" (½ mil) wire on an 18 percent neutral gray background. The EVT-1 standard as well as other known visual inspection standards rely on personal evaluation by an operator to ensure that the imaging system is providing the appropriate image quality to the remote display from which the inspection is performed.

During an IVVI inspection, the imaging system is evaluated by providing an appropriately sized wire on an appropriate gray background with predetermined and controlled lighting. The operator views the received image and determines the adequacy of the quality of the visual inspection system before proceeding with the IVVI inspection. As such, the assessment of the image quality, and therefore, the IVVI inspection of the nuclear reactor for flaws and damage, are entirely subjective and are therefore inconsistent over time and by operator. Any inconsistencies can result in the failure of the visual inspection system in providing an image for viewing in which the operator can identify a potential flaw or damage which can result in failure to identify such, or can require re-inspection, and therefore added time and costs for the IVVI inspection.

SUMMARY

The inventor hereof has succeeded at designing systems and methods for quantitatively and objectively assessing the quality of the imaging or visual inspection system in operating environments. These systems and methods are capable of providing, in some embodiments, partial or full automation of standardized rating of an imaging system, such as rating of the resolution and contrast of the imaging system or components thereof, improved consistency in image quality, improved inspection accuracy and confidence, improved operating system safety, and/or reduced costs for imaging system assessment and use.

According to one aspect, a system for quantitative image quality assessment of an imaging system includes a target, an image capture device and a computer. The target includes one or more image features with varying spatial resolutions and predetermined spatial frequencies and the image capture device is configured to capturing an image of the target. The computer includes a processor, a memory, and computer executable instructions. The computer is configured to receive the captured image of the target, prepare one or more intensity profiles across the captured image responsive to the predetermined spatial frequencies of the target, and determine a modulation transfer function in a spatial domain responsive to the one or more intensity profiles.

According to another aspect, a method for quantitatively assessing an imaging system includes placing a target having image features with varying spatial resolutions and predetermined spatial frequencies in view of an image capture device and capturing an image of the target. The method also includes preparing one or more intensity profiles across the captured target image and determining a modulation transfer function of contrast ratios in a spatial domain responsive to the spatial frequencies in the intensity profiles of the captured image.

According to yet another aspect, a system for quantitative image quality assessment of a nuclear reactor imaging system includes a target having one or more image features with varying spatial resolutions and predetermined spatial frequencies and an image capture device configured to inspect a component of a nuclear reactor and to capture an image of the target. A computer has a processor, a memory, and computer executable instructions and is configured to receive the captured image of the target, prepare one or more intensity profiles across the captured image responsive to the predetermined spatial frequencies of the target, and determine a modulation transfer function in a spatial domain responsive to the one or more intensity profiles.

According to still another aspect, a method for quantitatively assessing a nuclear reactor inspection imaging system includes placing a target having image features with varying spatial resolutions and predetermined spatial frequencies in view of an image capture device associated with the nuclear reactor inspection imaging system and capturing an image of the target. One or more intensity profiles are prepared across the captured image and a modulation transfer function of contrast ratios is determined in a spatial domain responsive to the spatial frequencies in the one or more intensity profiles of the captured image.

Further aspects of the present invention will be in part apparent and in part pointed out below. It should be understood that various aspects of the disclosure may be implemented individually or in combination with one another. It should also be understood that the detailed description and drawings, while indicating certain exemplary embodiments, are intended for purposes of illustration only and should not be construed as limiting the scope of the disclosure.

BRIEF DESCRIPTION OF THE DRAWINGS

It should be understood that throughout the drawings, corresponding reference numerals indicate like or corresponding parts and features.

DETAILED DESCRIPTION

The following description is merely exemplary in nature and is not intended to limit the present disclosure or the disclosure's applications or uses.

In some embodiments, a system or method for quantitatively assessing an imaging system includes placing a target having images of varying spatial resolutions and predetermined spatial frequencies in view of an image capture device and capturing an image of the target. The target typically includes black, white and one or more grey image features that define the varying spatial resolutions of predetermined spatial frequencies. However, in some embodiments, the target can include color images and the system can be configured to capture the color image and to assess a color resolution capability of the imaging system or to analyze the color information.

The method also includes preparing one or more intensity profiles across the captured target image and determining a modulation transfer function (MTF) of contrast ratios in a spatial domain responsive to the spatial frequencies in the one or more intensity profiles of the captured image. The determined modulation transfer function can be compared to a predetermined threshold or value set to determine an objective quality rating for the imaging system.

Figure 1:
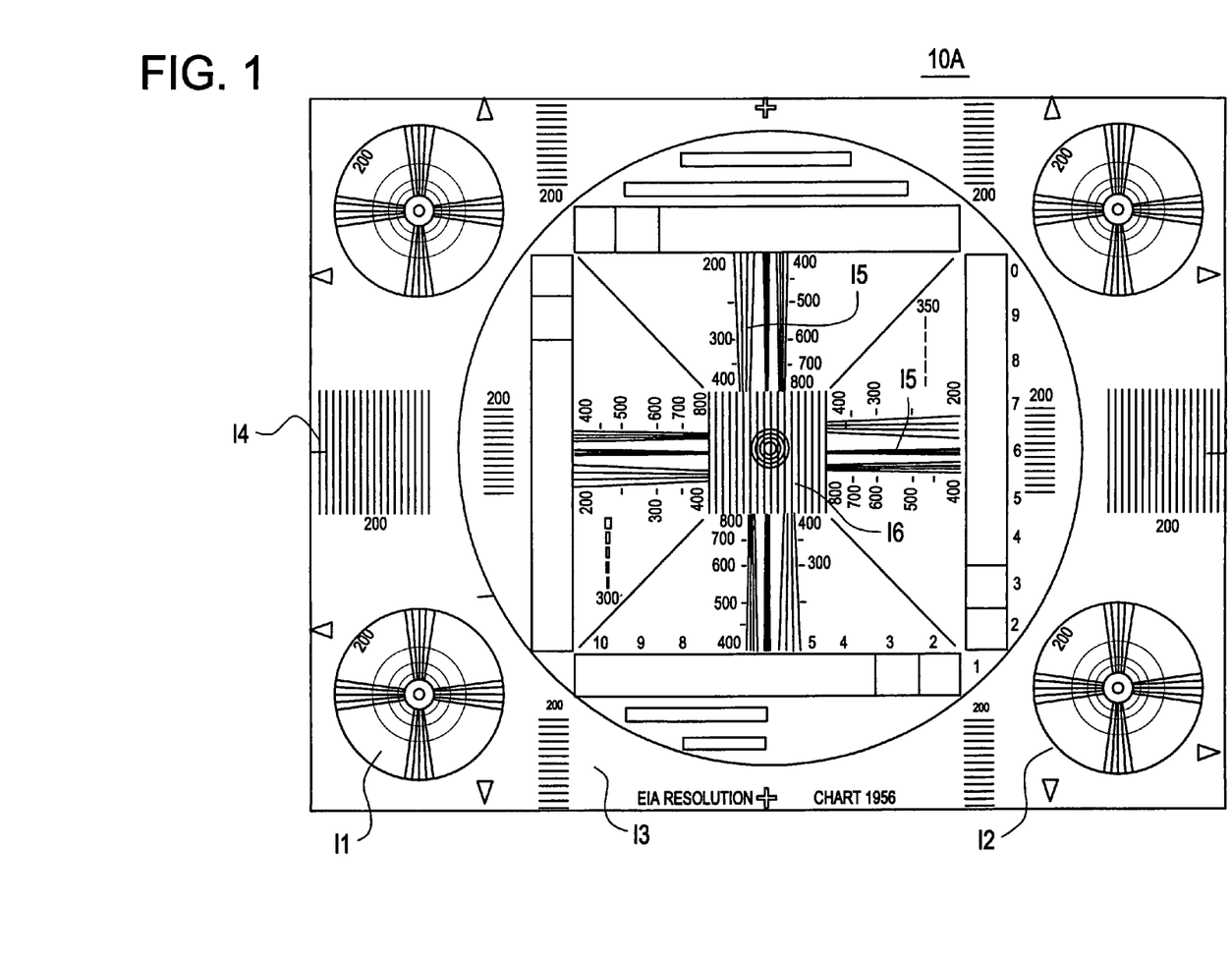
FIG. 1 is a view of a target having image features with varying spatial frequencies according to one exemplary embodiment.

The target includes one or more image, each with one or more image features having varying spatial resolutions and predetermined spatial frequencies. This can include, but is not limited to, a plurality of contrasting bars or sine wave patterns, having different widths, such as from zero (0) to one hundred (100) line pairs or more per distance measure, such as per millimeter. These can be in increasing or decreasing widths. These can include a plurality of repeating line sets of different widths of alternating white and black lines. Referring to FIG. 1, one example of a target 10A consistent with some embodiments is illustrated. This target 10 is available from the electronics industry association (EIA) in the United States. As shown, the target 10 includes several different images $I_N$ (denoted from $I_1$ to $I_6$) with each having a different spatial resolutions and predetermined spatial frequencies. As can be noted, a line drawn across the target or an image of the target will result in a variety of spatial resolutions. The target defines the predetermined spatial frequency that is known and utilized for each evaluation.

Figure 2:
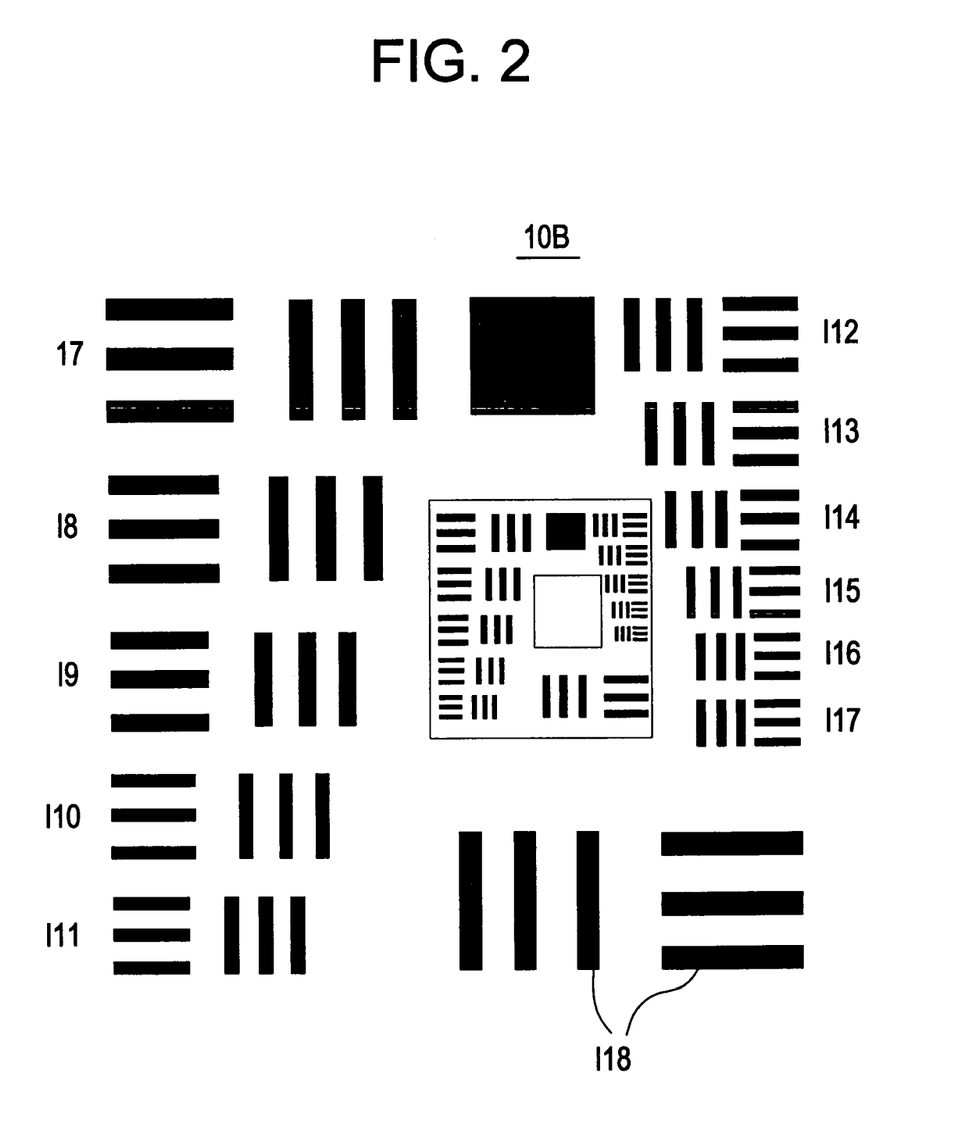
FIG. 2 is a view of an image for a target having varying spatial frequencies according to another exemplary embodiment.

FIG. 2 illustrates another example of a target 10B or an image of a target having a plurality of varying spatial resolutions and predetermined spatial frequencies. As indicated by the images indicated a $I_7$ to $I_{11}$ on the left, from $I_{12}$ to $I_{18}$ on the right, more than one image can be utilized for providing the different spatial resolutions as indicated by the different spacing between image lines, with each having a spatial frequency of the image lines.

Generally, targets will have a neutral grey background. Of course, as known to those skilled in the art, other types of targets and images for targets can also be developed that are suitable for displaying varying spatial resolutions of predetermined spatial frequencies.

The target can be movable and positionable in an operating environment of the image capture device. For example, in some embodiments it will be desirable to position the target relative to the image capture device to simulate the viewing of components during non-testing operation of the image capture device.

By utilizing the targets as describer herein, a transformation into the frequency domain, and all of the time consuming efforts associated with such a transformation are not required. For example, a target having images with varying spatial resolutions can be provided without requiring the use of edge-scanning of an image of a point source with a mechanical obscuration (knife-edge) during the monitoring of the intensity throughput as was previously required. Additionally, the current systems and methods do not require the use and positioning of a slit source and moving a pinhole or slit in the operating environment.

The image capture device can include a variety of components and systems. This can include any device capable of capturing an image and can include, by way of example, an analog camera, a digital camera having a CCD/CID lens, a digital camera having a semiconductor device, a digital camera having an optical lens train, and digital camera having a fiberscope. These can be either black and white image capture devices or can be color. Additionally, the image capture device can include a transmission facility or interface or a storage medium for communicating or storing images captured by the image capture device. The image capture device is configured and positionable relative to the target to capture the image of the target.

The image capture device is an electronic device for capturing an analog image of the target, further comprising an analog to digital converter for digitizing the analog target image. When the image capture device is an analog device, a frame grabber module or component of a computer system can be utilized to digitize the analog video signals. Frame grabbers are known in the art. The frame grabber need only have only enough memory to acquire or grab an image and store a single digitized video frame. In other embodiments, frame grabbers can include a substantial portion of memory for storing vast numbers of images. In fact, current versions can not only acquire longer video sequences, but are also capable of compressing the video sequences in real time using algorithms such as MPEG. The frame grabber generally should be capable of sampling an image at a high enough density to preserve all spatial frequencies contained in the target image. For example, it should be able to sample at least two times the highest spatial frequency (i.e., the Nyquist sampling rate) in the image for preserving the spectral content and reducing losses and/or distortions due to the A/D conversion. Generally, frame grabbers perform the opposite function of a typical graphics adapter.

In one exemplary embodiment, a support system can include a circuit to recover the horizontal and vertical synchronization pulses from the input signal and an analog-to-digital converter. NTSC/SECAM/PAL color decoder circuit and/or software can be provided as well as an ample supply of memory for storing the acquired image. This can include, in some embodiments, a frame buffer. An interface, such as a bus or serial interface is utilized by a main processor to control data acquisition and to access the data.

The image capture device can be in a fixed position or can be movable in an operating environment. In the later embodiment, the image capture device can be positioned to not only capture images from within the operating environment, such as images of components or items therein, but also the target and its images.

The line scanning can be performed by a computer configured with line-scan software and for preparing intensity profiles to measure the contrast ratios across the intensity profiles at the predetermined spatial frequencies.

An intensity profile of an image is a set of intensity values from points along a line segment in an image. The intensity profile is an analytical line profile tool. The intensity profile is typically based on the width of the line chosen, the wider or broader the line, the more image captured and therefore the higher the intensity. As such, it can be desirable to maintain a consistent line width.

To create the intensity profile, the intensity values along the line segments are calculated and can be plotted. This requires a prior definition of the one or more line segments based on their coordinates within the image. The line segment can be any line segment or line through any portion of the image, at any orientation. These are generally regularly spaced points along the line. The line can be automatically identified, manually determined or interactively determined. In some embodiments, the same lines along the target image are used for quality assessment tests. Typically a peak and valley of the intensity profile corresponds to the light and dark bands in an image. The measurement and/or determination of the contrast ratios can be fully automated for determination by a computer. In some embodiments, a plot of the contrast ratios at two or more predetermined spatial frequencies can be prepared. In such embodiments, the modulation transfer function can be determined in the spatial domain by utilizing the plot. An intensity profile can be plotted as a distance along the line segment from a beginning to an end on the x-axis and an intensity value on the y-axis.

The line scan function can be provided by software that is configured to measure contrast ratios across the digitized target image. Line scan software can include Genesis Multipoint Automated Advanced Linescan by EDAX, Inc. which is a part of AMETEK, Inc.; Thermographic Software IRBIS® linescan by InfraTec; and Esprit LineScan from Burker-axs.

The intensity profile is taken across the digitized image of the target. The intensity profile is a profile of the intensity across one or more selected lines through the image. This selected line can be at conjugate, on axis or off axis positions. Generally, a line scan is a line-by-line series of horizontal slices that can be extracted directly from the images without a need to transform into the frequency spectrum as is typically done. Thereafter, the intensity profile from the digital or digitized image is analyzed to determine contrast ratios at the various predetermined spatial frequencies.

MTF is a measurement of the ability of the imaging system to transfer levels of detail from an object into an image. The MTF is the contrast ratio measured (e.g., the modulation) at various spatial frequencies. Generally, as is known in the art, a transfer function is associated with a system where a response or output is related to an input. The modulation transfer function (MTF) as addressed herein is the amount of contrast resolution that is provided in the output image as a result of an input image and the transfer function of the imaging system. MTF is the spatial frequency response of an imaging system or a component; it is the contrast at a given spatial frequency relative to low frequencies. High spatial frequencies correspond to fine image detail. The more extended the response, the finer the detail and the sharper the image.

Spatial frequency is typically measured in cycles or line pairs per millimeter (lp/mm), which is analogous to cycles per second (Hertz) in audio systems. While the MTF can be developed by transformation to the frequency domain, the current systems and methods do not require such a transformation. As described herein, the MTF determined from the line scans are determined in the spatial domain, rather than requiring a transformation into the frequency domain. The measured contrast ratios at the predetermined spatial frequencies can be plotted as points on the MTF (as a curve or mathematical function or formula) for any particular one of the spatial frequencies. This plotting is typically plotting the contrast or measured contrast amount as a percentage versus the spatial frequency in lp/mm. For the plot, the x-axis having representing the MTF is typically normalized to a value of 1 at zero spatial frequency, e.g., all white or all black.

It should be noted that this MTF plotting is different than an MTF plot associated with a lens or camera design. In those cases, an MTF chart typically plots the contrast ratio as a function of the distance from the center of the lenses with a different plot for one or more (typically two) spatial frequencies, one at a low spatial frequency indicative of contrast reproduction capability of a lens and a second curve at a higher spatial frequency indicative of the resolving power or sharpness of the lens. In these cases, the quality of the lens from the center towards the outer edges indicates the flat response or reproduction capabilities of the lens, e.g., the flatter both curves are from the center of the lens to the outer edges, the higher quality of the lens.

Figure 3:
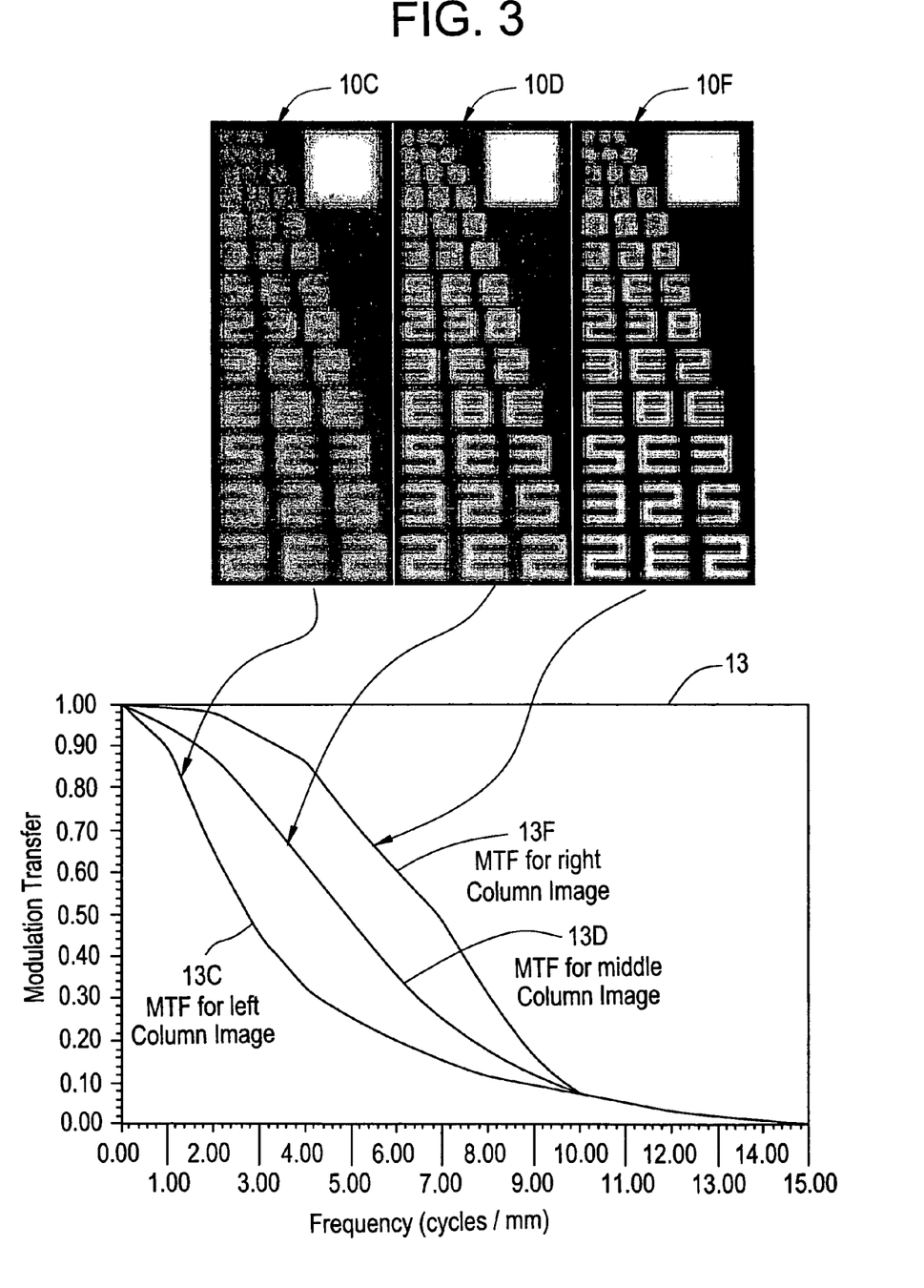
FIG. 3 is a view of three image with varying spatial frequencies and a plot of their modulation transfer function according to one exemplary embodiment.

FIG. 3 illustrates one exemplary embodiment of three different target images having image features that define varying spatial resolutions of predetermined spatial frequencies. The images 10C, 10D, and 10F each produce a different modulation transfer function MTF, 11C, 11D and 11F, respectively, as indicated in plot 11 by the three different plotted lines. It should be noted that a point higher on the plot or chart is indicative of a higher contrast transfer capability of the imaging system. In other words, the MTF plot is higher on the x-axis when more contrast is transferred from the image to the reproduction of the image by the imaging system.

In some embodiments, a nuclear reactor imaging system is configured to inspect a component of the nuclear reactor and to capture the image of the target during an assessment of the quality of the imaging system. These can include in-vessel visual inspection systems and enhanced visual inspection systems. The target and image capture device are each configured to be positioned within a pool of the nuclear reactor during operation.

Figure 4:
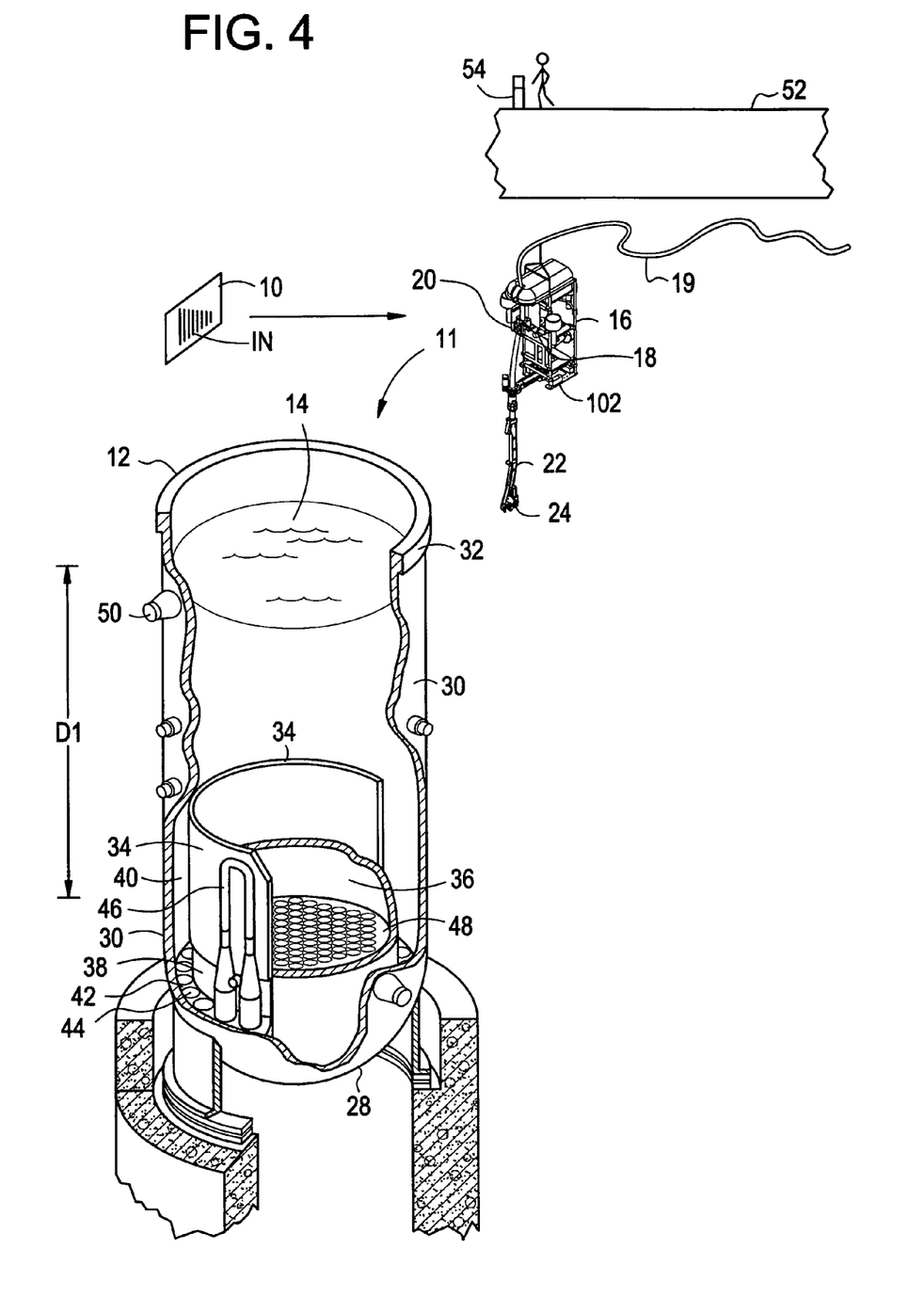
FIG. 4 is a cut-away side view of a reactor pressure vessel and a target having an image with varying spatial frequencies and imaging system for quantitatively assessing the quality of the imaging system according to one exemplary embodiment.

One such exemplary embodiment is illustrated in FIG. 4. A reactor 11 includes a reactor pressure vessel (RPV) 12 that is filled with a pool 14 of liquid, such as water. The nuclear reactor 11 has one or more bores in which a remote inspection device 16 is to be delivered. One of the features of the remote inspection device 16 is its imaging capabilities. The operator is dependent on the imaging system for operation and maneuvering the remote inspection device 16 within the pool 14. Additionally, one or more main inspection camera 18, or other image capturing device, can be positioned on the remote inspection device and provide image signal over a transmission facility 19 (wired or wireless). Such camera 18 can include, in some embodiments, a wide angle, a zoom capability, and a tilt and rotation capability. These can be both a black and white and a color camera.

Additionally, the remote inspection device 16 can include one or more illumination or lighting devices (lights) 20 for illuminating portions of the RPV 10 to be viewed or imaged by the camera. The illumination system 20 should be configured to selectively provide an illumination on the target during the capturing of the image of the target during imaging system testing. Such illumination should be repeatable from one operation to a next over an operating period to provide consistent lighting on the target 10 and/or between the target 10 and the image capture device 18. The illumination system lights 20 can be controllable in intensity and focus and can be, in some embodiments, positioned in an off axis position relative to the image capture device or camera 18, and can provide polychromatic lighting or otherwise. Such controlled illumination can provide for a controlled illumination of the target image that simulates the controlled illumination in the operating environment.

The remote inspection device 16 can also include an inspection probe 22 that can be extendable from a main body of the remote inspection device 16 and positionable within a remote location including positioning within a bore of a pipe or an aperture to be visually inspected. The inspection probe 22 can include a camera 24 as well as one or more other sensors or inspection devices as are known in the art.

For clarity purposes only, FIG. 4 illustrates a sectional view, with parts cut away, of the boiling water nuclear reactor pressure vessel (RPV) 12. Typically, during operation the RPV 12 includes additional items including fuel and control rods and a cover which are not shown in FIG. 3 as FIG. 3 illustrates the RPV 12 during a maintenance procedure such as a refuel procedure. As such, some components have been removed and are not shown. However, this is a typical situation where a visual inspection device 16 is delivered within the pressure vessel 12 and to submerged reactor components such as pipes and bores for inspecting welds, by way of example.

The RPV 12 can have a generally cylindrical shape and is closed at one end by a bottom head 28 and at its other end by a removable top head (not shown). A side wall 30 extends from bottom head to top. The side wall 30 includes a top flange 32 on which the top head (not shown) attaches. A cylindrically shaped core shroud 34 surrounds a reactor core 36. The shroud 34 is supported at one end by a shroud support 38 and includes a removable shroud head (not shown) at the other end. An annulus 40 is formed between shroud 34 and side wall 30. A pump deck 42, which has a ring shape, extends between shroud support 38 and the side wall 30. In some embodiments, the pump deck 42 includes a plurality of circular openings 44 with each opening housing a jet pump assembly 46 (only one is shown in FIG. 3 for clarity purposes). The jet pump assemblies 46 are circumferentially distributed around core shroud 34.

In operation of the reactor 10, heat is generated within core 36, which includes fuel bundles of fissionable material (not shown). Fuel bundles are aligned by a core plate 48 located at the base of core 36. Water is circulated up through core 36 and core plate 48 and is at least partially converted to steam. The steam exits the RPV 12 through a steam outlet 50 near top of the RPV 12.

As FIG. 3 illustrates the RPV 12 during a maintenance procedure, an operator can be positioned along a gangway, platform, or refuel bridge 52 and can operate an in vessel visual inspection (IVVI) system 54. The IVVI system 54 can include a user control interface such as a display, a joystick, a steering wheel, a mouse, a keyboard, a voice input, or other type of operator input for receiving an input from an operator. The IVVI system 54 generates control commands that are communicated to the inspection device 16 and receives the visual image signals via the transmission facility 19. The inspection device 16 is placed into the pool 14, which as shown may be within the RPV 12, and is moved within the pool 14 in response to received commands. As understood to those skilled in the art, FIG. 3 is not necessarily to scale and, as such, the size of the inspection device 16 as compared to the RPV 12 or components thereof may vary in other embodiments or implementations.

A target 10 is also positionable within the pool 14 of the RPV 12. The target 10 includes an image $I_N$ having varying spatial resolutions of predetermined spatial discrete frequencies. Examples of such a target 10 are provided in FIGS. 2, 3, and 4, as will be addressed below. The target 10 can be placed in a fixed position within pool 14 or can be movable within the pool 14 or other operating environment so as to provide for real world operating objective assessment of the imaging systems quality. In one exemplary embodiment, the target 10 can be affixed to a portion of the inspection device 16 and viewable by camera 18 or 24. In some embodiments, the target 10 is positioned relative to receive light from light 20 having a predefined and/or controllable intensity and direction. In such embodiments, such lighting and viewing can be standardized for each viewing or can be adapted to various predefined levels so as to simulate or duplicate a planned viewing by camera 18 or 24 of a reactor component or feature.

In operation, the target 10 is placed in the reactor 11 in a working position so that the imaging system 18 can be evaluated during testing and/or calibration. For example, the target 10 can be placed in the reactor pool 14 before each use of the inspection system 16 and its imaging system, at the end of each use, and/or at specified intervals. For example, it may be desirable that the quality of the imaging system be evaluated every 4 hours of imaging system use.

In one exemplary inspection operation, the inspection device 16 is controlled to propel it into the RPV 12 and down to a distance of D1 that is between the side wall 30 and the shroud 34. In other words, the inspection probe 22 with camera 18 can be positioned in various positions within the RPV 10, including the annulus 40 containing the jet pump assemblies 46, by way of example. The inspection device 16 can be temporarily attached to a component in the RPV 10 to stabilize the inspection device 16 during a visual inspection. The inspection device 16 is later detached and moved to another jet pump assembly 46 or reactor component and another inspection is then preformed. As is also apparent to those skilled in the art, the inspection device 16 can include one or more camera 18 for inspection of the outward portions of the reactor components and/or can include the camera 24 attached to the extendable probe 22 for insertion into a bore such as the bore of the jet pump assembly 46.

As discussed above, the inspection device 16 is controlled by an operator or the IVVI system 54 with one or more of the thrusters for moving the inspection device 16 within the pool 14. The inspection device 16 is moved and positioned within the pool 14 such that the inspection probe 22 is positionable within the pool 14 and possibly for insertion into a bore and positioning of camera 24 therein. Once so positioned, the camera 24 is manipulated to provide remotely viewed images for remote visual display, storage and therefore inspection. Once a first component such as the jet pump assembly 46 has been inspected, the inspection probe 22 with camera 24 is removed and the inspection device 16 is moved via remote control commands to another position within the RPV 10 for inspecting another reactor component.

Figure 5:
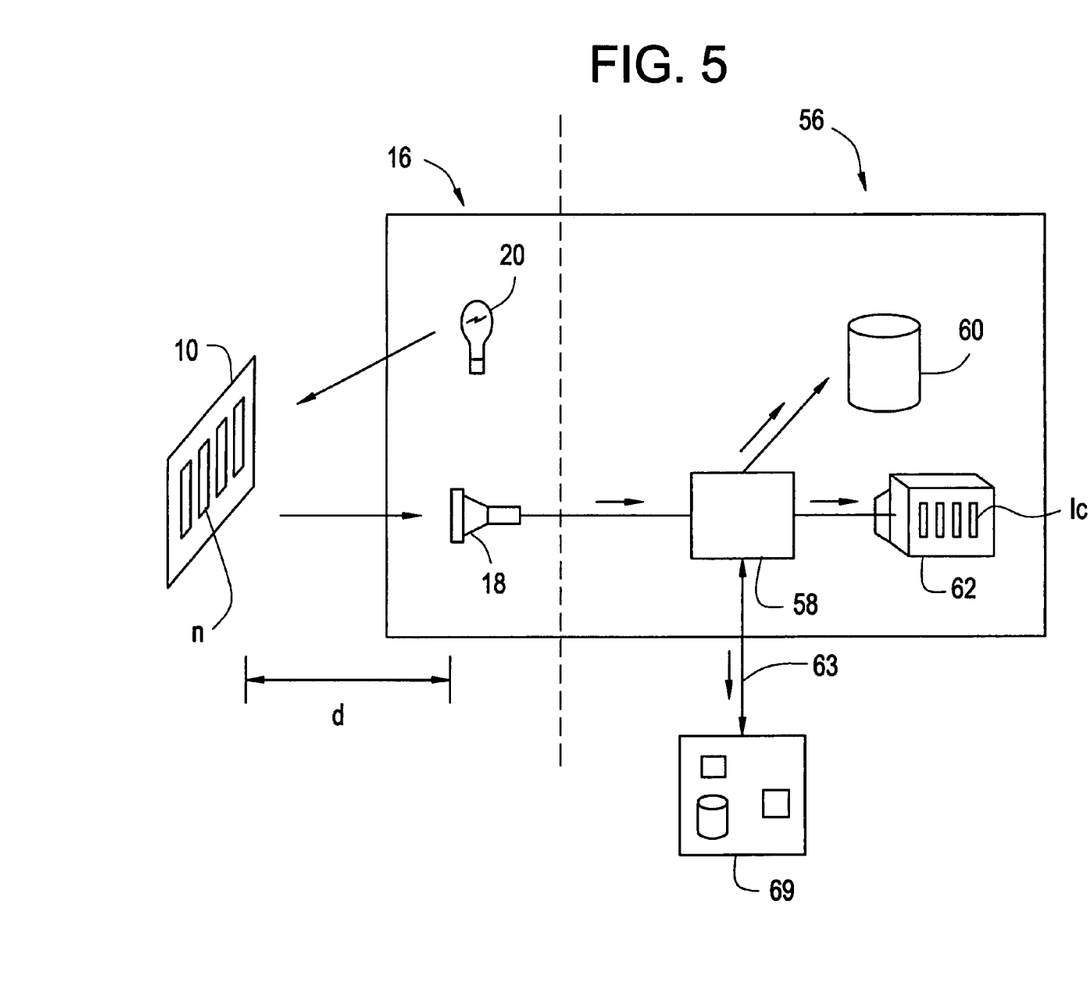
FIG. 5 is a block diagram of a system for quantitatively assessing the quality of an imaging system according to another exemplary embodiment.

Referring now to FIG. 5, in one exemplary embodiment, a system 56 that is configured for quantitative image quality assessment includes the target 10 having images $I_N$ as described above. The image capture device 18 is positioned at a distance d from the target 10 and the illumination device 20 illuminates the target 10 and image $I_N$. The image capture device 18 provides a captured image to a computer 58. The system 56 can also includes a memory system 60, an output device 62 (such as a display for displaying the captured image $I_C$, and computer executable instructions including the line scan software and instruction for implementing one or more of the methods and/or processes as described above. The MTF can be displayed locally to a system operator, for example. An output interface 63 can also be provided for transmitting the captured image $I_C$, the line scan, the determined MTF or a related analysis to a remote system 64.

The memory system 60 can provide for either recording the images or transmitting them to a remote system or device. The image data can be recorded in a standard digital format such as an MPEG file format or equivalent. This can provide for a stored record of the calibration and system acceptance. Additionally, some or all of the IVVI examination can be recorded to provide a digitally archive of the examination.

In other embodiments, the computer can be configured to compare the determined modulation transfer function of the captured image to a predetermined threshold such as defined by a design, regulatory or other system specification. The predetermined threshold can be defined as a percent modulation at a minimum desired spatial frequency equal to about one thousand (1,000) 1p/in, by way of example. In some embodiments, the percent modulation can be equal to or greater than a predefined minimum level of about fifty (50) percent modulation that equate to about 50 percent contrast ratio, by way of example. Such thresholds can be established based on known system requirements, testing specifications, regulations or other standards and practices as necessary for evaluation of the imaging system. The modulation transfer function threshold can be determined as a function of a variety of parameters including one or more contrast ratios and one or more modulations. For IVVI systems, the MTF can be determined to equate to a spatial resolution of a 0.5 millimeter diameter wire on an eighteen (18) percent neutral grey background as a typical standard used by IVVI systems.

Figure 6:
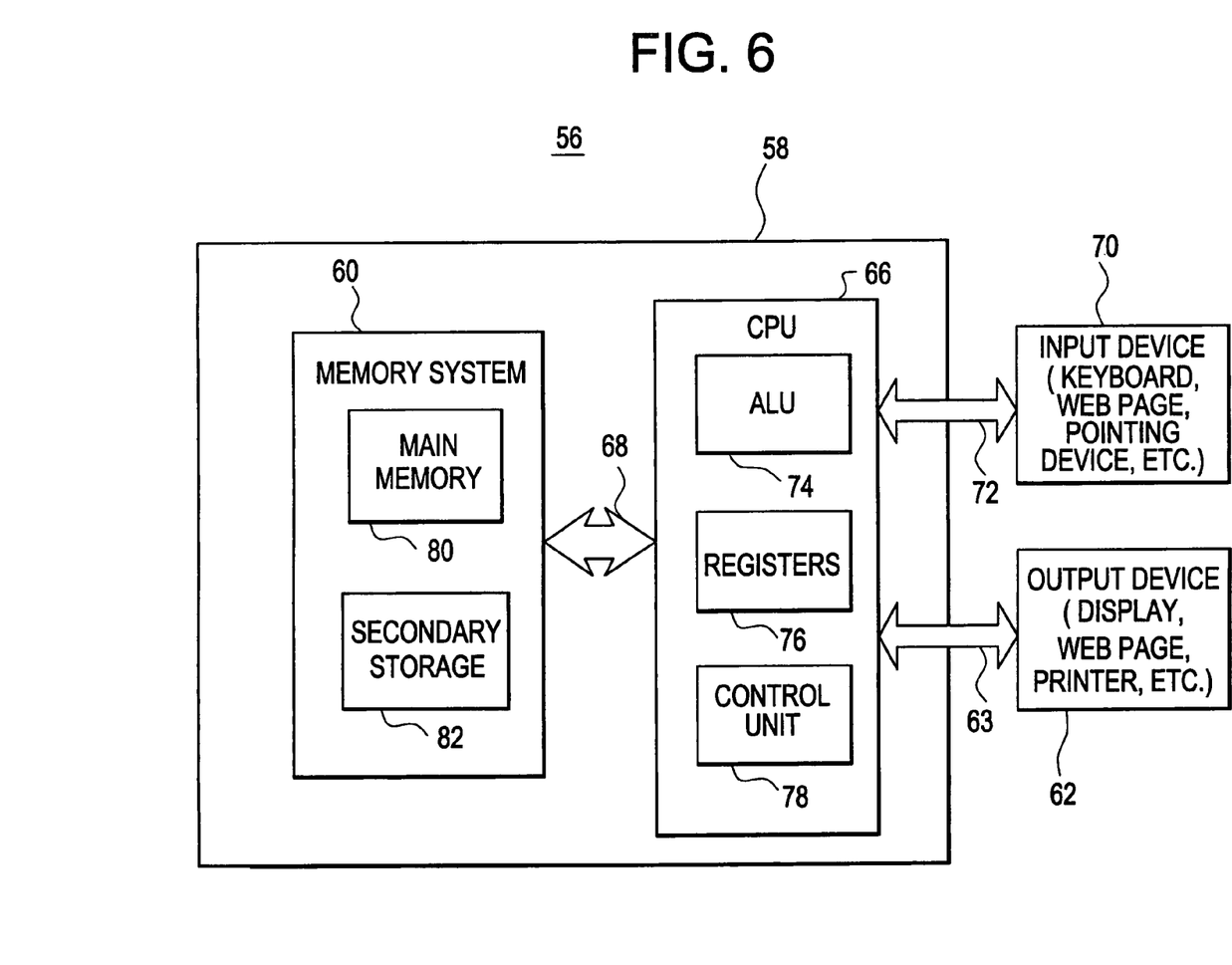
FIG. 6 is a block diagram of an exemplary computer system that can be used to implement some embodiments or components of the systems and/or methods for quantitatively assessing images and/or an imaging system.

One such exemplary computer operating environment for some embodiments for quantitatively assessing the quality of images produced by an imaging system is shown by way of example in FIG. 6. As shown in FIG. 6, in this example of system 56, one or more computers 58 each can have at least one high speed processing unit (CPU) 66, in conjunction with the memory system 60 interconnected with at least one bus structure 68, an input 70, and an output 62.

The input 70 and output 62 are familiar and can be implemented associated with the local and remote user interfaces as well as a controller, remote operational system and operations system, by way of example. The input 70 can include a keyboard, a mouse, a physical transducer (e.g. a microphone), or communication interface or port, by way of example, and is interconnected to the computer 58 via an input interface 72. The output 62 can includes a display, a printer, a transducer (e.g. a speaker), output communication interface or port, etc, and be interconnected to the computer 58 via an output interface 63. Some devices, such as a network adapter or a modem, can be used as input and/or output devices.

The illustrated CPU 66 is of familiar design and includes an arithmetic logic unit (ALU) 74 for performing computations, a collection of registers 76 for temporary storage of data and instructions, and a control unit 78 for controlling operation of the system 56. Any of a variety of processors, including at least those from Digital Equipment, Sun, MIPS, Motorola/Freescale, NEC, Intel, Cyrix, AMD, HP, and Nexgen, is equally preferred for the CPU 66. The illustrated embodiment of the disclosure operates on an operating system designed to be portable to any of these processing platforms.

The memory system 60 generally includes high-speed main memory 80 in the form of a medium such as random access memory (RAM) and read only memory (ROM) semiconductor devices, and secondary storage 82 in the form of long term storage mediums such as floppy disks, hard disks, tape, CD-ROM, flash memory, etc. and other devices that store data using electrical, magnetic, optical or other recording media. The main memory 80 also can include a video display memory for displaying images through a display device. Those skilled in the art will recognize that the memory system 60 can comprise a variety of alternative components having a variety of storage capacities.

As is familiar to those skilled in the art, the system 56 can further include an operating system and at least one application program (not shown). The operating system is the set of software which controls the computer system's operation and the allocation of resources. The application program is the set of software that performs a task desired by the user, using computer resources made available through the operating system. Both are resident in the illustrated memory system 60. As known to those skilled in the art, some of the methods, processes, and/or functions described herein can be implemented as software and stored on various types of computer readable medium as computer executable instructions. In various embodiments of the systems and methods for quantitatively assessing the quality of an image produced by an imaging system described by example herein, the computer system 56 can include a robust operating and application program having the computer executable instructions for performing one or more of the above processes. Additionally, one or more of the local and remote user interfaces, operations system and remote operations system can include, among other application software programs with computer executable instructions, a thin client application for communicating and interactively operating with one or more controllers as described above by way of example.

In accordance with the practices of persons skilled in the art of computer programming, the present disclosure is described below with reference to symbolic representations of operations that are performed by the system 56. Such operations are sometimes referred to as being computer-executed. It will be appreciated that the operations which are symbolically represented include the manipulation by the CPU 66 of electrical signals representing data bits and the maintenance of data bits at memory locations in the memory system 60, as well as other processing of signals. The memory locations where data bits are maintained are physical locations that have particular electrical, magnetic, or optical properties corresponding to the data bits. The disclosure can be implemented in a program or programs, comprising a series of instructions stored on a computer-readable medium. The computer-readable medium can be any of the devices, or a combination of the devices, described above in connection with the memory system 60.

It should be understood to those skilled in the art, that some embodiments of systems or components for quantitatively assessing the quality of an image produced by an imaging system, as described herein, can have more or fewer computer processing system components and still be within the scope of the present disclosure. Additionally, while the example embodiments described herein have general application within in vessel visual inspections systems for nuclear reactors, it should be understood that the disclosed embodiments can also be applied in other applications and operating environments. For example, these can include any type of visual testing non-destructive examination (VT-NDE) process or system, any type of video image quality assessment, camera manufacturer objective image quality ratings, broadcaster and service provide (cable TV, satellite or otherwise), scientific imaging including astronomy, medical imaging such as digital radiography, ultrasound, MRI, CT, and PET, or any other visual imaging system where high resolution and high contrast my be critical to system performance.

When describing elements or features and/or embodiments thereof, the articles "a", "an", "the", and "said" are intended to mean that there are one or more of the elements or features. The terms "comprising", "including", and "having" are intended to be inclusive and mean that there may be additional elements or features beyond those specifically described.

Those skilled in the art will recognize that various changes can be made to the exemplary embodiments and implementations described above without departing from the scope of the disclosure. Accordingly, all matter contained in the above description or shown in the accompanying drawings should be interpreted as illustrative and not in a limiting sense.

It is further to be understood that the processes or steps described herein are not to be construed as necessarily requiring their performance in the particular order discussed or illustrated. It is also to be understood that additional or alternative processes or steps may be employed.

What is claimed is:

1. A system for quantitative image quality assessment of an imaging system, comprising:
    a target having one or more image features with varying spatial resolutions and predetermined spatial frequencies;
    an image capture device configured to capture an image of the target; and
    a computer having a processor, a memory, and computer executable instructions and configured to receive the captured image of the target, prepare one or more intensity profiles across the captured image responsive to the predetermined spatial frequencies of the target, and determine a modulation transfer function in a spatial domain responsive to the one or more intensity profiles.

2. The system of claim 1, wherein the imaging system is a nuclear reactor imaging system,
    wherein the target and image capture device are each configured for positioning within a pool of a nuclear reactor, and
    wherein the image capture device is configured to inspect a component of the nuclear reactor and to capture the image of the target during an assessment of the quality of the imaging system.

3. The system of claim 2, wherein the nuclear reactor imaging system includes an in-vessel visual inspection system or an enhanced visual inspection system.

4. The system of claim 1, wherein the image capture device includes an analog camera, a digital camera having a CCD/CID lens, a digital camera having a semiconductor device, a digital camera having an optical lens train, or a digital camera having a fiberscope.

5. The system of claim 1, further comprising:
    an illumination system having an illumination device and a control system for controlling the illumination device;
    wherein the illumination system is configured to selectively illuminate the target during the capture of the image of the target.

6. The system of claim 1, further comprising:
    an analog-to-digital converter;
    wherein the image capture device is an electronic device for capturing an analog image of the target, and
    wherein the analog-to-digital converter digitizes the captured analog image.

7. The system of claim 6, wherein the analog-to-digital converter includes computer executable instructions for an image frame grabber.

8. The system of claim 1, wherein the computer includes line-scan software having the computer executable instructions for preparing the one or more intensity profiles measuring contrast ratios across the one or more intensity profiles, and
    wherein the computer is further configured to prepare the one or more intensity profiles and to assign the measured contrast ratios to the predetermined spatial frequencies.

9. The system of claim 8, wherein the computer is further configured to utilize the line-scan software for measuring the contrast ratios at two or more of the predetermined spatial frequencies.

10. The system of claim 9, wherein the computer is further configured to plot the contrast ratios at the two or more predetermined spatial frequencies, and
    wherein the modulation transfer function is responsive to the plot.

11. The system of claim 1, wherein the computer is further configured to compare the determined modulation transfer function to a predetermined threshold.

12. The system of claim 11, wherein the predetermined threshold is defined as a percent modulation at a minimum desired spatial frequency equal to about 1,000 line pairs per inch (lp/in).

13. The system of claim 12, wherein the percent modulation is equal to or greater than a predefined minimum level of about fifty percent.

14. The system of claim 12, wherein the predetermined threshold is responsive to at least one of a contrast ratio and a modulation, and
    wherein the predetermined threshold is determined responsive to a spatial resolution of a 0.5 millimeter diameter wire on an 18 percent neutral grey background.

15. The system of claim 1, wherein the image capture device is a digital device configured for capturing a digital image of the target, and wherein the computer is further configured to receive the captured digital image from the image capture device.

16. The system of claim 1, wherein the captured target image is communicated to the computer by an image transfer system, and wherein the image transfer system includes a data communication facility or a computer readable medium.

17. The system of claim 1, wherein the target includes black, white, and one or more grey image features defining the varying spatial resolutions and predetermined spatial frequencies.

18. The system of claim 1, wherein the target includes one or more image features having color, and wherein the computer is further configured to assess a color resolution capability of the imaging system.

19. The system of claim 1, wherein the computer is further configured to receive and store the captured image from the image capture device, the prepared one or more intensity profiles, and the determined modulation transfer function.

20. A system for quantitative image quality assessment of a nuclear reactor imaging system, comprising:

a target having one or more image features with varying spatial resolutions and predetermined spatial frequencies;

an image capture device configured to inspect a component of a nuclear reactor and to capture an image of the target; and a computer having a processor, a memory, and computer executable instructions and configured to receive the captured image, prepare one or more intensity profiles across the captured image responsive to the predetermined spatial frequencies of the target, and determine a modulation transfer function in a spatial domain responsive to the one or more intensity profiles.

21. A method for quantitatively assessing an imaging system, comprising:

placing a target having one or more image features with varying spatial resolutions and predetermined spatial frequencies in view of an image capture device;

capturing an image of the target;

preparing one or more intensity profiles across the captured target image; and determining a modulation transfer function of contrast ratios in a spatial domain responsive to the predetermined spatial frequencies in the one or more intensity profiles.

22. The method of claim 21, further comprising:

illuminating the target with a controlled illumination during capturing of the image.

23. The method of claim 21, further comprising:

comparing the determined modulation transfer function to a predetermined threshold for quantitatively assessing a quality of the imaging system.

24. The method of claim 23, further comprising:

placing the image capture device in a pool of a nuclear reactor for capturing the image of the target; and quantitatively rating a quality of a nuclear reactor inspection imaging system in response to the comparing;

wherein the image capture device is associated with the nuclear reactor inspection imaging system, and wherein placing the target includes placing the target in the pool of the nuclear reactor.

25. The method of claim 23, wherein the predetermined threshold is greater than or equal to a minimum desired spatial frequency of about fifty percent modulation at about 1,000 line pairs per inch (lp/in).

26. The method of claim 23, further comprising:

determining a contrast ratio threshold responsive to a resolution of a wire against a neutral grey background.

27. The method of claim 21, further composing:

measuring contrast ratios at two or more of the predetermined spatial frequencies.

wherein the target includes one or more images defining the predetermined spatial frequencies.

28. The method of claim 27, further comprising:

plotting the measured contrast ratios at the two or more predetermined spatial frequencies;

wherein plotting the measured contrast ratios and determining the modulation transfer function are responsive to preparing the one or more intensity profiles.

29. The method of claim 21, further comprising:

digitizing the captured target image.

30. The method of claim 21, further comprising:

assessing a color resolution of the imaging system.

31. The method of claim 21, further comprising:

receiving and storing the captured image, the prepared one or more intensity profiles, and the determined modulation transfer function.

32. A method for quantitatively assessing a nuclear reactor inspection imaging system comprising:

placing a target having image features with varying spatial resolutions of predetermined spatial frequencies in view of an image capture device of a nuclear reactor inspection imaging system positioned within a nuclear reactor;

capturing an image of the target;

preparing one or more intensity profiles across the captured image;

determining a modulation transfer function of contrast ratios responsive to the predetermined spatial frequencies in the one or more intensity profiles; and comparing the determined modulation transfer function in a spatial domain to a predetermined threshold for quantitatively assessing a quality of the nuclear reactor inspection imaging system.

* * * * *